(12) United States Patent
Mital et al.

(10) Patent No.: US 7,758,676 B2
(45) Date of Patent: Jul. 20, 2010

(54) ADAPTIVE LEARNING METHOD FOR CLEAN PARTICULATE FILTER PRESSURE DROP

(75) Inventors: Rahul Mital, Rochester Hills, MI (US); Chad E. Marlett, Plymouth, MI (US); James R Ireton, Jr., Brighton, MI (US); Thomas E Wiseman, Canton, MI (US)

(73) Assignee: GM Global Technology Operations, Inc.

( * ) Notice: Subject to any disclaimer, the term of this patent is extended or adjusted under 35 U.S.C. 154(b) by 650 days.

(21) Appl. No.: 11/542,688

(22) Filed: Oct. 3, 2006

(65) Prior Publication Data
US 2008/0078236 A1 Apr. 3, 2008

(51) Int. Cl.
*B01D 59/26* (2006.01)
(52) U.S. Cl. .................... 96/113; 95/15; 95/19; 96/114; 96/161; 96/417; 96/421; 96/422; 55/DIG. 34; 702/47
(58) Field of Classification Search .............. 95/15, 95/19; 96/113, 114, 161, 417, 421, 422; 55/DIG. 34
See application file for complete search history.

(56) References Cited

U.S. PATENT DOCUMENTS

| 4,803,838 | A  | * | 2/1989  | Kaeser ......................... 60/288 |
| 5,287,698 | A  | * | 2/1994  | Shinzawa et al. ............. 60/286 |
| 6,405,528 | B1 | * | 6/2002  | Christen et al. ............... 60/295 |
| 6,622,480 | B2 | * | 9/2003  | Tashiro et al. ................. 60/295 |
| 6,829,890 | B2 | * | 12/2004 | Gui et al. ...................... 60/295 |
| 2002/0033017 | A1 | * | 3/2002 | Bruggemann et al. ......... 60/295 |
| 2004/0211159 | A1 | * | 10/2004 | Hamahata et al. .......... 55/282.3 |
| 2005/0150221 | A1 | * | 7/2005 | Crawley et al. ............... 60/295 |

FOREIGN PATENT DOCUMENTS

| CN | 1568400 A | 1/2005 |
| DE | 69004159 T2 | 3/1994 |
| DE | 102004025436 A1 | 12/2005 |
| DE | 602004000466 T2 | 5/2006 |

* cited by examiner

*Primary Examiner*—Robert J Hill, Jr.
*Assistant Examiner*—Christopher P Jones

(57) ABSTRACT

A control system for particulate filters is provided. The control system for a particulate filter includes a clean filter estimating module that estimates a clean pressure based on a first pressure in the particulate filter within a predetermined period of a regeneration event. A soot prediction module estimates a level of soot in the particulate filter based on a comparison of the first pressure and a second pressure in the particulate filter received after the predetermined period.

15 Claims, 4 Drawing Sheets

ADAPTIVE LEARNING METHOD FOR CLEAN PARTICULATE FILTER PRESSURE DROP

FIELD

The present disclosure relates to methods and systems for particulate filter regeneration systems.

BACKGROUND

The statements in this section merely provide background information related to the present disclosure and may not constitute prior art.

Diesel engines typically have higher efficiency than gasoline engines due to an increased compression ratio and a higher energy density of diesel fuel. A diesel combustion cycle produces particulates that are typically filtered from diesel exhaust gas by a particulate filter (PF) that is disposed in the exhaust stream. Over time, the PF becomes full and the trapped diesel particulates must be removed. During regeneration, the diesel particulates are burned within the PF. As emission standards increase, it is anticipated that particulate filters may be used in non-diesel applications as well.

Conventional methods initiate regeneration based on distance driven, time since last regeneration, fuel burnt, or predicted soot accumulation. Newer methods evaluate a pressure drop in the particulate filter to initiate regeneration. These methods use one or more predetermined tables to predict a pressure drop. The pressure entries in the predetermined tables are typically determined from nominal parts. Therefore, variations in the substrate of the particulate filters, variations in sensor properties, and various affects due to ash accumulation are not accounted for in the tables. This results in reduced accuracy in the prediction of soot in the filter.

For example, when there is a low limit part, the methods under predict the soot loading on the filter resulting in risk to the hardware during regeneration. When there is a high limit part, the methods over predict the soot loading on the filter resulting in too frequent regenerations which impacts fuel economy. The conventional methods also do not take into account variability of the accumulation based on drive cycle characteristics. Thus, the method has proven to be unreliable.

SUMMARY

Accordingly, a control system for particulate filters is provided. The control system includes a clean filter estimating module that estimates a clean pressure based on a first pressure in the particulate filter within a predetermined period of a regeneration event. A soot prediction module estimates a level of soot in the particulate filter based on a comparison of the first pressure and a second pressure in the particulate filter received after the predetermined period.

In other features, a method of estimating soot levels in a particulate filter is provided. The method includes: receiving a first pressure in the particulate filter within a predetermined period of a regeneration event; estimating a clean pressure based on the first pressure in the particulate filter; receiving a second pressure in the particulate filter after the predetermined period of the regeneration event; and estimating a level of soot in the particulate filter based on a comparison of the first pressure and the second pressure.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
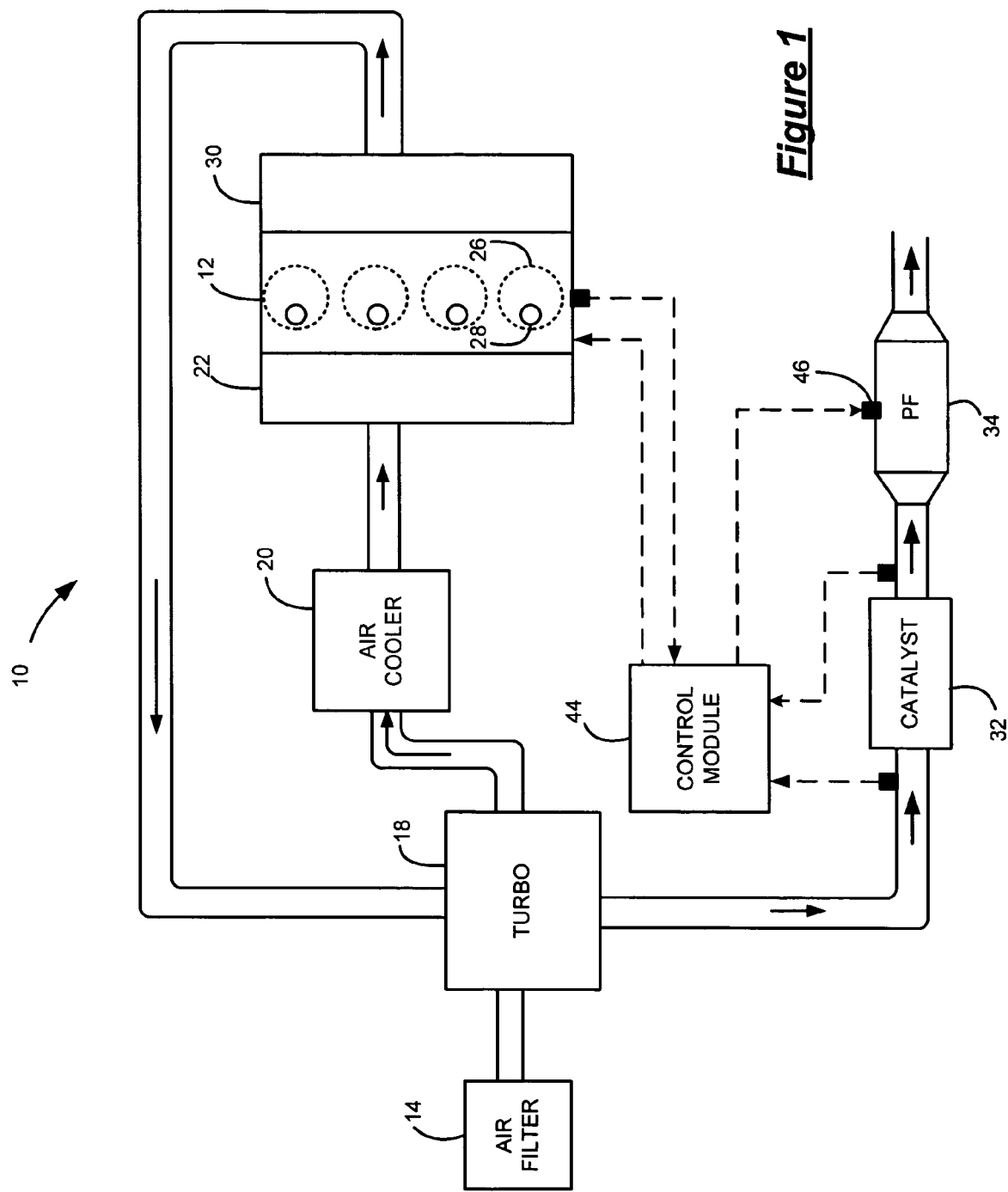
FIG. 1 is a functional block diagram of a vehicle including a particulate filter.

The following description is merely exemplary in nature and is not intended to limit the present disclosure, application, or uses. It should be understood that throughout the drawings, corresponding reference numerals indicate like or corresponding parts and features. As used herein, the term module refers to an application specific integrated circuit (ASIC), an electronic circuit, a processor (shared, dedicated, or group) and memory that executes one or more software or firmware programs, a combinational logic circuit, and/or other suitable components that provide the described functionality.

Referring now to FIG. 1, an exemplary diesel engine system 10 is schematically illustrated in accordance with the present invention. It is appreciated that the diesel engine system 10 is merely exemplary in nature and that the adaptive pressure drop measurement system described herein can be implemented in various engine systems implementing a particulate filter. Such engine systems may include, but are not limited to, gasoline direct injection engine systems and homogeneous charge compression ignition engine systems. For ease of the discussion, the remainder of the disclosure will be discussed in the context of a diesel engine system.

A turbocharged diesel engine system 10 includes an engine 12 that combusts an air and fuel mixture to produce drive torque. Air enters the system by passing through an air filter 14. Air passes through the air filter 14 and is drawn into a turbocharger 18. The turbocharger 18 compresses the fresh air entering the system 10. The greater the compression of the air generally, the greater the output of the engine 12. Compressed air then passes through an air cooler 20 before entering into an intake manifold 22.

Air within the intake manifold 22 is distributed into cylinders 26. Although four cylinders 26 are illustrated, it is appreciated that the systems and methods of the present invention can be implemented in engines having a plurality of cylinders including, but not limited to, 2, 3, 4, 5, 6, 8, 10 and 12 cylinders. It is also appreciated that the systems and methods of the present invention can be implemented in a v-type cylinder configuration. Fuel is injected into the cylinders 26 by fuel injectors 28. Heat from the compressed air ignites the air/fuel mixture. Combustion of the air/fuel mixture creates exhaust. Exhaust exits the cylinders 26 into the exhaust system.

The exhaust system includes an exhaust manifold 30, a diesel oxidation catalyst (DOC) 32, and a particulate filter (PF) 34. Optionally, an EGR valve (not shown) re-circulates a portion of the exhaust back into the intake manifold 22. The remainder of the exhaust is directed into the turbocharger 18 to drive a turbine. The turbine facilitates the compression of the fresh air received from the air filter 14. Exhaust flows from the turbocharger 18 through the DOC 32 and the PF 34. The DOC 32 oxidizes the exhaust based on the post combustion air/fuel ratio. The amount of oxidation increases the temperature of the exhaust. The PF 34 receives exhaust from the DOC 32 and filters any soot particulates present in the exhaust.

A control module 44 controls the engine and PF regeneration based on various sensed information. A first pressure sensor senses a differential in pressure of exhaust gases flowing through the PF and generates a first pressure sensor signal accordingly. As can be appreciated, other sensors and methods may be employed to sense or determine a pressure differential in the PF 34. The control module 44 receives the pressure sensor signal and determines a PF pressure drop based on drop measurement methods and systems as will be discussed further below. The control module 44 thereafter estimates loading of the PF 34 based on the pressure drop. When the estimated loading achieves a threshold level (e.g., 5 grams/liter of particulate matter) and the exhaust flow rate is within a desired range, the regeneration process is initiated. The duration of the regeneration process varies based upon the amount of particulate matter determined to be within the PF 34.

Figure 2:
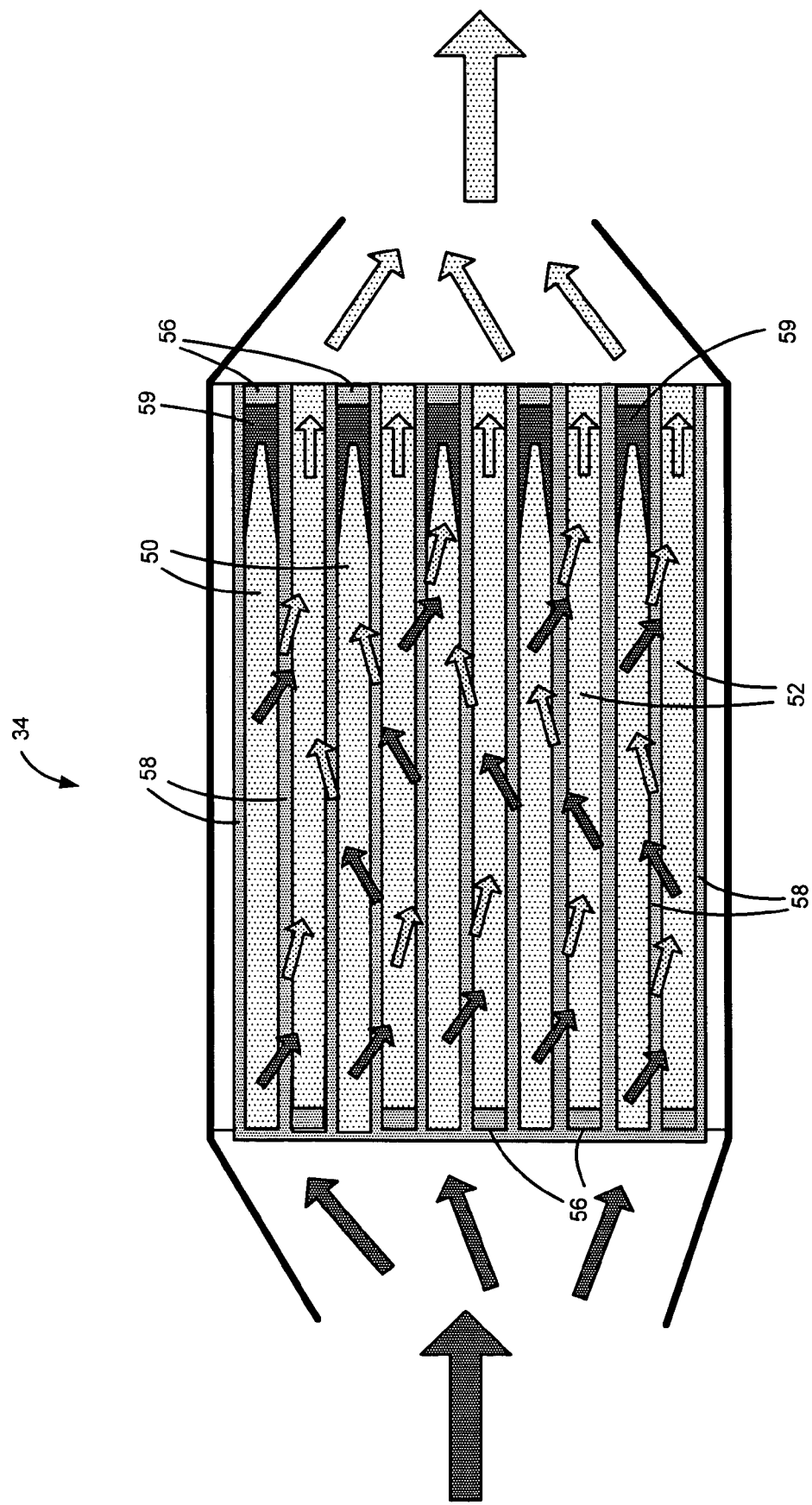
FIG. 2 is a cross-sectional view of a wall-flow monolith particulate filter.

With particular reference to FIG. 2, an exemplary PF 34 is shown. The exemplary PF 34 is a monolith particulate trap and includes alternating closed cells/channels 50 and opened cells/channels 52. The cells/channels 50,52 are typically square cross-sections, running axially through the part. Walls 58 of the PF 34 are preferably comprised of a porous ceramic honeycomb wall of cordierite material. It is appreciated that any ceramic comb material is considered within the scope of the present invention. Adjacent channels are alternatively plugged at each end as shown at 56. This forces the diesel aerosol through the porous substrate walls which act as a mechanical filter. Particulate matter is deposited within the closed channels 50 and exhaust exits through the opened channels 52. Soot particles 59 flow into the PF 34 and are trapped therein. An accumulation of the soot particles impacts the pressure drop in the PF 34.

Figure 3:
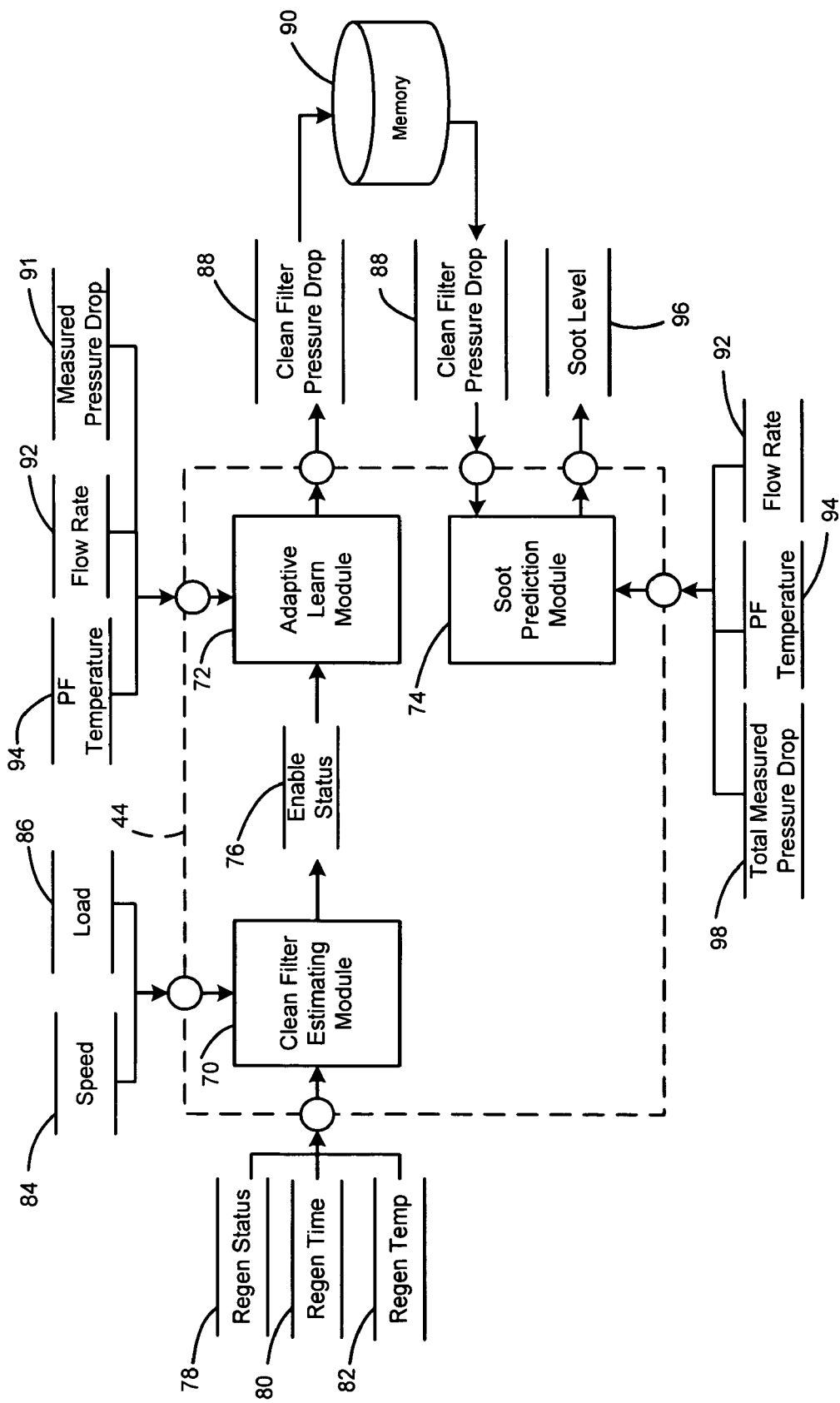
FIG. 3 is a dataflow diagram illustrating an adaptive pressure drop measurement system.

With reference to FIG. 3, a dataflow diagram illustrates various embodiments of an adaptive pressure drop measurement system that may be embedded within the control module 44. Various embodiments of adaptive pressure drop measurement systems according to the present disclosure may include any number of sub-modules embedded within the control module 44. The sub-modules shown may be combined and/or further partitioned to similarly measure a pressure drop of the PF 34. Inputs to the system may be sensed from the system 10 (FIG. 1), received from other control modules (not shown) within the system 10 (FIG. 1), and/or determined by other sub-modules (not shown) within the control module 44. In various embodiments, the control module 44 of FIG. 3 includes a clean filter estimating module 70, an adaptive learn module 72, and a soot prediction module 74.

The clean filter estimating module 70 monitors regeneration event conditions to determine when the PF 34 is clean and sets an enable status flag 76 accordingly. In various embodiments, the clean filter estimating module 70 monitors a regeneration time 80, a regeneration temperature 82, and a regeneration complete status indicator 78 to ensure that regeneration has completed and that the PF 34 is clean. For example, if the regeneration status indicator 78 indicates that regeneration is complete, the regeneration time 80 indicates that regeneration occurred for a predetermined time, and the regeneration temperature 82 indicates that the PF temperature was equal to or above a predetermined temperature threshold during regeneration, the PF 34 is deemed clean and the enable status flag 76 is set to TRUE. Otherwise, the enable status flag 76 remains set to FALSE.

As can be appreciated, the clean filter estimating module 70 may also monitor engine system enable conditions to determine an appropriate time to perform an adaptive learn once the PF 34 is clean. Such engine system enable conditions can include, but are not limited to, speed 84 and load 86. For example, if the speed 84 and load 86 conditions are within predetermined ranges respectively, the enable status flag 76 is set to TRUE. Otherwise, the enable status flag 76 remains set to FALSE.

The adaptive learn module 72, once enabled via the enable status flag 76, adaptively learns pressure drop values 88 and stores the values in memory 90 for later use. In various embodiments, a pressure drop value 91 for a given flow rate 92 and PF temperature 94 is measured once the PF 34 is clean. The measured pressure drop 91 is then stored as clean filter pressure drop 85 in a two-dimensional clean pressure drop table accessed by PF temperature 94 and volume flow rate 92. The soot prediction module 74 estimates a level of soot 96 in the PF 34 based on a total measured pressure of the PF 98, values 88 from the clean filter pressure table, a PF temperature 94, and a volume flow rate 92. More particularly, the soot prediction module 74 measures at total pressure drop 98 across the PF 34; and retrieves a clean pressure drop 88 from the clean filter table based on PF temperature 94 and volume flow rate 92. Based on the total pressure drop (TP) 98, the clean pressure drop (CP) 88, and the flow rate 92, the soot prediction module 74 computes a resistance flow rate (RF) as shown by the following equation:

$$RF=(TP-CP)/FR \quad (1)$$

The soot prediction module 74 then uses the computed resistance flow to determine a soot accumulation level 96. In various embodiments, a soot accumulation level 96 is estimated based on a two-dimensional lookup table defined by the volume flow rate 92 and the resistance flow.

Figure 4:
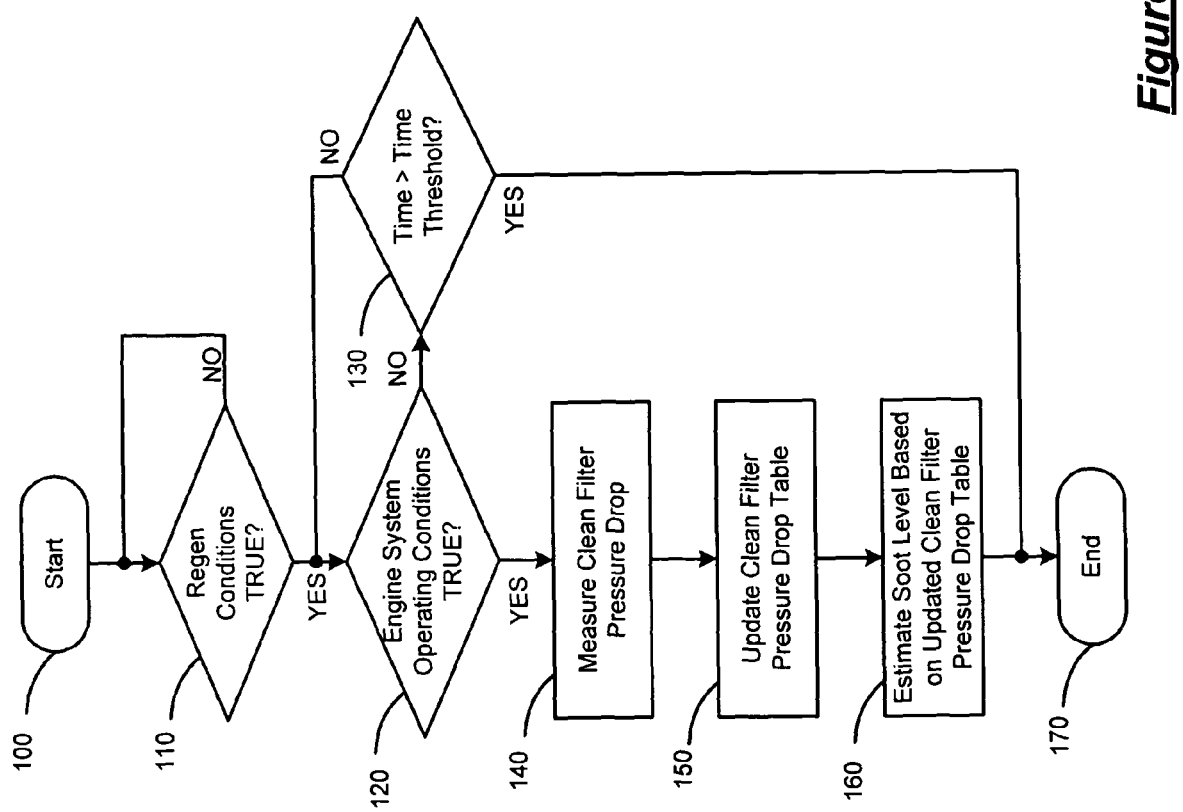
FIG. 4 is a process flow diagram illustrating an adaptive pressure drop measurement method.

With reference to FIG. 4, a process flow diagram illustrates various embodiments of an adaptive pressure drop measurement method that may be performed by the control module 44 of FIG. 3. As can be appreciated, the method may be run periodically during engine operation. The method begins at 100. At 110, regeneration complete enable conditions are evaluated. If the regeneration complete enable conditions are TRUE at 110, engine system operating conditions are evaluated at 120. Otherwise, control loops back and continues to monitor regeneration complete enable conditions at 110. If the engine system operating conditions are TRUE at 120, the clean filter pressure drop is measured and stored in memory at 130. Otherwise, control loops back and continues to monitor engine system enable conditions at 120. As can be appreciated, if control continues to monitor engine system enable conditions for too long after the regeneration is complete at 130, so as too accumulate soot in the PF, control proceeds to the end. Otherwise, once the clean filter pressure drop is measured and stored in memory at 130 and 140 respectively, control estimates the soot accumulation in the PF at 150 based on a resistance flow rate and a volume flow rate as discussed above. As can be appreciated, the soot estimation at 150 can be performed at various times during engine operation and is not limited to the sequential execution as shown in FIG. 4.

Those skilled in the art can now appreciate from the foregoing description that the broad teachings of the present disclosure can be implemented in a variety of forms. Therefore, while this disclosure has been described in connection with particular examples thereof, the true scope of the disclosure should not be so limited since other modifications will become apparent to the skilled practitioner upon a study of the drawings, specification, and the following claims.

What is claimed is:

1. A control system for a particulate filter, comprising:
   an adaptive lean module that selectively stores a first pressure drop across the particulate filter when an engine enable condition is met within a predetermined period after a regeneration event;
   a clean filter estimating module that monitors the engine enable condition and that estimates a clean pressure drop based on the first pressure drop across the particulate filter;
   a soot prediction module that estimates a level of soot in the particulate filter based on a comparison of the clean pressure drop and a second pressure drop across the particulate filter,
   wherein the second pressure drop is measured after the predetermined period; and
   a module that initiates a next regeneration event based on the level of soot.

2. The system of claim 1 wherein the soot prediction module estimates a level of soot in the particulate filter based on a difference between the second pressure drop and the clean pressure drop.

3. The system of claim 1 wherein the regeneration event is determined based on a regeneration period, a regeneration status indicator, and a regeneration temperature.

4. The system of claim 1 wherein the engine enable condition is met when at least one of a speed is within a predetermined range and a load is within a predetermined range.

5. The system of claim 4 wherein the adaptive learn module selectively stores the first pressure drop for a given flow rate and particulate filter temperature.

6. The system of claim 5 further comprising memory and wherein the adaptive learn module stores the first pressure drop in a lookup table in the memory wherein the lookup table is accessed by the corresponding flow rate and particulate filter temperature.

7. The system of claim 1 wherein the clean filter estimating module estimates the clean pressure drop based on the first pressure drop when engine enable conditions are met, and wherein the engine enable conditions are based on at least one of speed and load.

8. The system of claim 1 wherein the clean filter estimating module estimates the clean pressure drop based on the first pressure drop when engine enable conditions are met, and wherein the engine enable conditions are based on a time since the regeneration event.

9. The system of claim 1 wherein the soot prediction module estimates the level of soot in the particulate filter based on a resistance flow wherein the resistance flow is estimated from the second pressure drop, the clean pressure drop, and a flow rate.

10. The system of claim 9 wherein the soot prediction module estimates the level of soot in the particulate filter based on a lookup table accessed by the resistance flow and the flow rate.

11. The system of claim 1 further comprising a pressure sensor disposed within the particulate filter that generates a first pressure signal and a second pressure signal.

12. The system of claim 1 wherein the soot prediction module determines a resistance flow rate based on the comparison and determines the level of soot accumulated within the particulate filter based on the resistance flow rate.

13. The system of claim 12 wherein the soot prediction module determines the resistance flow rate based on a difference between the total pressure drop and the clean pressure drop.

14. The system of claim 13 wherein the soot prediction module determines the resistance flow rate based on a quotient of the difference and a volume flow rate.

15. The system of claim 12 wherein the soot prediction module estimates the level of soot accumulated within the particulate filter based on a lookup table defined by volume flow rate and the resistance flow rate.

* * * * *